United States Patent [19]
Ferrari

[11] Patent Number: 5,973,169
[45] Date of Patent: Oct. 26, 1999

[54] IPRIFLAVONE PREPARATION PROCESS

[75] Inventor: Massimo Ferrari, Cenate Sotto, Italy

[73] Assignee: Erregierre S.p.A., San D'Argon, Italy

[21] Appl. No.: 09/255,043

[22] Filed: Feb. 22, 1999

[30] Foreign Application Priority Data

Mar. 10, 1998 [IT] Italy .................................. MI98A0483

[51] Int. Cl.⁶ .................................................. C07D 311/55
[52] U.S. Cl. ............................................ 549/406; 549/408
[58] Field of Search ...................... 549/406, 408

[56] References Cited

U.S. PATENT DOCUMENTS 3,340,276  9/1967  Carney et al. ........................ 260/345.2

FOREIGN PATENT DOCUMENTS

0478558B1  2/1994  European Pat. Off. .
1027007   11/1978  Italy .

Primary Examiner—James H. Reamer
Attorney, Agent, or Firm—Abelman, Frayne & Schwab

[57] ABSTRACT

Process for the preparation of ipriflavone consisting in the following steps:
a) reaction of 2,4-dihydroxy-phenyl-benzyl-ketone of formula (II) with ethyl orthoformate in dimethylformamide as solvent and in the presence of a catalyst consisting of morpholine, to yield 7-hydroxyisoflavone of formula (III),
b) separation of product (III) from the reaction residue,
c) alkylation of product (III) from step b) with isopropyl halide to obtain ipriflavone, wherein:
  I. step a) is carried out at a temperature ranging from 115 to 120° C. using a 2,4-dihydroxy-phenyl-benzyl-ketone (II) weight/solvent volume (w/v) ratio lower than 1:4;
  II. step b) consists in the precipitation of the corresponding salt with dicyclohexylamine of formula (IV).

The process yields 7-hydroxyisoflavone (III) in high yields within short reaction times (2 h max.) and ipriflavone with impurity ≦0.1%.

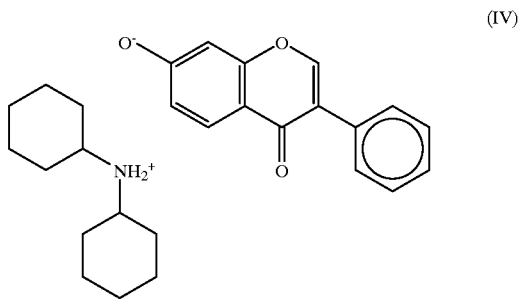

(IV)

5 Claims, No Drawings

IPRIFLAVONE PREPARATION PROCESS

FIELD OF THE INVENTION

The present invention refers to a process for the preparation of ipriflavone.

STATE OF THE ART

Ipriflavone of formula (I)

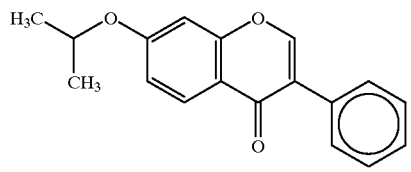

(I)

is a calcium regulator especially used in human therapy for the treatment of osteoporosis.

Italian patent 1027007 discloses processes for ipriflavone preparation according to the following schemes.

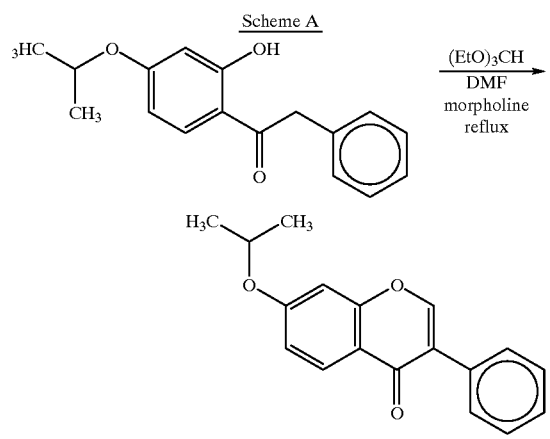

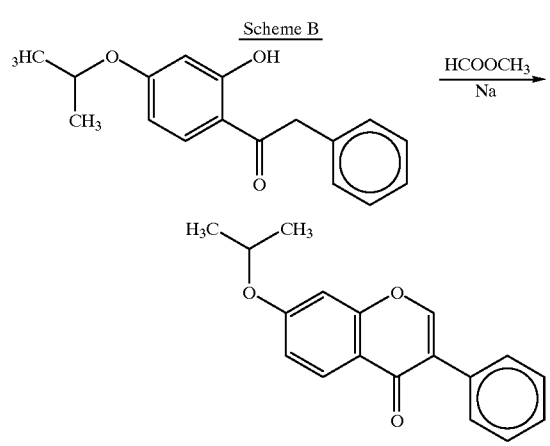

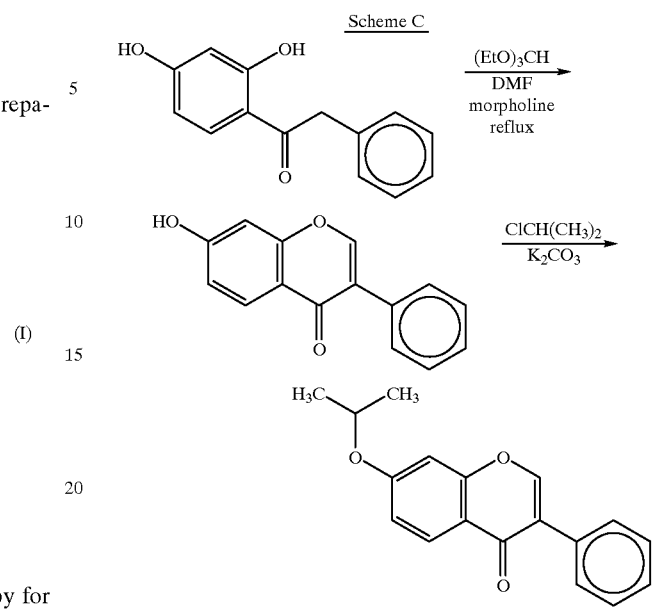

As envisaged in the aforementioned Italian patent as well as in U.S. Pat. No. 3,340,276, ring closing, according to Scheme C, takes place at a temperature ranging from 110 to 150° C., in the presence of a mixture of solvents selected from the group consisting of dimethylformamide, pyridine and a secondary amine, such as morpholine, piperidine, pyrrolidine. At the boiling point of said mixture, the ethanol that forms can be distilled off during the reaction to enhance the conversion or increase the temperature.

However, a non-negligible inconvenience of Scheme C is that, during ring closing, i.e. in the first reaction, there is the formation of large quantities (from 2 to 10%) of by-product 7-ethoxyisoflavone of formula V:

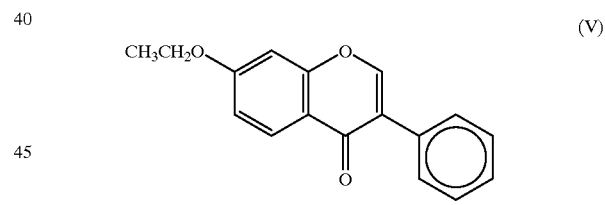

(V)

Said by-product can be removed from intermediate 7-hydroxyisoflavone exclusively through repeated treatments with various solvents.

To make up for this inconvenience, patent EP-0-478-558B1 describes that ring closing takes place at lower temperatures (ranging from 70 to 100° C.) and in the presence of decidedly small volumes of solvent (dimethylformamide or isopropanol), i.e. 0.3 to 2 times the weight of reagent 2,4-dihydroxy-phenyl-benzyl-ketone (II), or in the presence of ethyl orthoformate only.

Under the conditions of this patent, product (III) is formed in oversaturation concentrations ranging from 20 to 70% by wt. of the weight of the solution.

The product obtained in 90% yield is 7-hydroxyisoflavone (III) containing 0.2 to 0.5% 7-ethoxyisoflavone as impurity.

The impurity content can decrease to 0.1% if reaction product (III) is separated from the reaction mixture as a salt of formula:

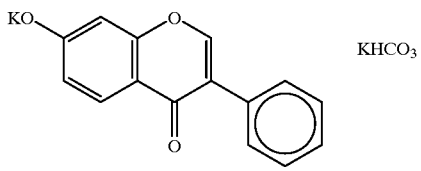

This process is an undoubted improvement on the known processes for ipriflavone preparation; however, the long time (5 to 16 h) taken for the preparation of intermediate (III) is its chief drawback.

SUMMARY

The Applicant has now surprisingly found a process for ipriflavone preparation making up for the drawbacks of the prior art.

In particular, the process of the invention, in analogy with the processes of the prior art reported in Scheme C, comprises in the following steps:
- a) reaction of 2,4-dihydroxy-phenyl-benzyl-ketone of formula (II) with ethyl orthoformate in dimethylformamide as solvent and in the presence of a catalyst consisting of morpholine, to yield 7-hydroxyisoflavone of formula (III),
- b) separation of product (III) from the reaction residue,
- c) alkylation of product (III) from step b) with isopropyl halide to obtain ipriflavone.

However, the process of the invention differs from the processes of the prior art because:
- I. step a) is carried out at a temperature ranging from 115 to 120° C. using a 2,4-dihydroxy-phenyl-benzyl-ketone (II) weight/solvent volume (w/v) ratio lower than 1:4;
- II. product (III) is separated by precipitation of the corresponding salt with dicyclohexylamine of formula (IV)

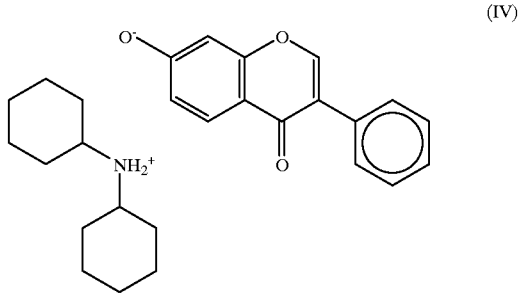

If step a) is carried out at 115–120° C. and with the aforementioned solvent ratios by vol., product (III) will be obtained within times in the order of 2 h, i.e. much shorter than the times required by the processes of the prior art. Furthermore, by operating under said conditions, it is possible to obtain product (III) contaminated with only 2% of 7-ethoxyisoflavone. The recovery of salt (IV) allows the obtainment of 7-hydroxyisoflavone having a content of by-product 7-ethoxyisoflavone of 0.1% max., with a stoichiometric yield ranging from 80 to 85%.

DETAILED DESCRIPTION OF THE INVENTION

Step a) of the process of the invention is preferably carried out using 2,4-dihydroxy-phenyl-benzyl-ketone (II) weight/solvent volume (w/v) ratios ranging from 1:5 to 1:7.

Once step a) has been completed, the reaction solvent is distilled.

Salt (IV) is preferably prepared by dissolving the residue from the distillation of the reaction solvent (step a) with sec-butyl alcohol and toluene at a temperature ranging from 40 to 50° C., at which temperature dicyclohexylamine is added.

Salt (IV) is converted again to 7-hydroxyisoflavone in an acid environment at pH preferably ranging from 2 to 3. It is particularly preferred to use a water/sec-butyl alcohol/othophosphoric acid mixture in a ratio equal to 6:3:1 by wt.

The following example is conveyed by way of indication, not of limitation, of the process of the invention.

EXAMPLE 1A

Preparation of 7-hydroxyisoflavone 2,4-Dihydroxy-phenyl-benzyl-ketone (II) (228 g; 1 mol) was dissolved in dimethylformamide (1400 g). The solution was added with morpholine (40 g; 0.46 mol) and triethyl orthoformate (180 g; 1.21 mol).

The reaction mixture was heated to 115–120° C. for 2 h and followed by TLC (eluents: chloroform/methanol/ammonia 75/20/2.5 by vol.) or until disappearance of the spot due to starting product (II).

The solvents present in the reaction mixture consisting of dimethylformamide, the ethanol formed during the reaction, and excess ethyl orthoformate were evaporated under vacuum.

HPLC analysis showed that the reaction crude mainly consisted of product (III) and approx. 2% of 2-ethoxyisoflavone (V).

EXAMPLE 1B

Preparation of Salt (IV)

The residue from the distillation described in Example 1A was dissolved in sec-butyl alcohol and toluene, added with dicyclohexylamine (approx. 200 g). The resulting reaction mixture was cooled. Salt (IV) precipitated therefrom was filtered and washed with water.

EXAMPLE 1C

Preparation of Pure 7-hydroxyisoflavone

The salt obtained in Example 1B was treated at 70° C. with water (600 g), sec-butyl alcohol (300 g) and 85% orthophosphoric acid (100 g). The precipitate obtained was filtered and dried in an oven at a temperature of 80° C. for 6 h.

7-Hydroxyisoflavone (195 g) with 0.1% max. impurity consisting of 7-ethoxyisoflavone was obtained. The stoichiometric reaction yield was 82%.

EXAMPLE 1D

Preparation of Ipriflavone (I)

7-Hydroxyisoflavone (35 kg), dimethylformamide (35 kg), potassium carbonate (35 kg) and isopropyl bromide (25 kg) were fed to a reactor.

The reaction mass was heated to 70° C. for 6 h and added, at said temperature, with sec-butyl alcohol (90 kg) and water (300 kg). Then it was cooled. The solid was filtered and washed with water. The wet solid was dissolved in ethanol (200 kg) at boiling. The solution was cooled and the solid precipitate was filtered, washed with ethanol and dried at 70° C.

39.7 kg of 7-isopropoxy-isoflavone was obtained.
Stoichiometric yield =96.6%.
Chromatographic purity: (HPLC) ≧99.9%.
7-Ethoxyisoflavone ≦0.1%.

I claim:
1. Process for the preparation of ipriflavone comprising the following steps:
   a) reacting 2,4-dihydroxy-phenyl-benzyl-ketone of formula (II)

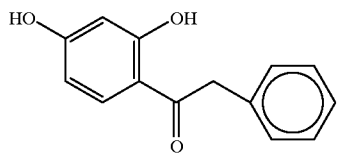

(II)

with ethyl orthoformate in dimethylformamide as solvent and in the presence of a catalyst consisting of morpholine, to yield 7-hydroxyisoflavone of formula (III)

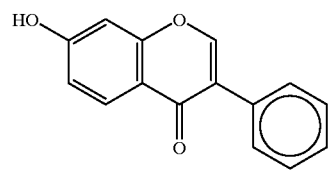

(III)

b) separating of product (III) from the reaction residue,
   c) alkylating of product (III) from step b) with isopropyl halide to obtain ipriflavone, wherein:
      I. step a) is carried out at a temperature ranging from 115 to 120° C. by using a 2,4-dihydroxy-phenyl-benzyl-ketone (II) weight/solvent volume (w/v) ratio lower than 1:4;
      II. step b) consists in the precipitation of the corresponding salt with dicyclohexylamine of formula (IV)

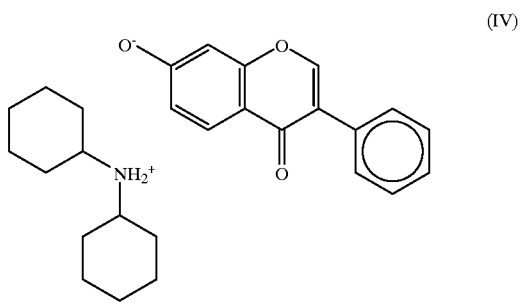

(IV)

2. The process as claimed in claim 1, wherein step a) of the process of the invention is carried out by using a 2,4-dihydroxy-phenyl-benzyl-ketone (II) weight/solvent volume (w/v) ratios ranging from 1:5 to 1:7.

3. The process as claimed in claim 1, wherein step b) is carried out by dissolving the residue from the distillation of the reaction solvent of step a) in water, sec-butyl alcohol and toluene at a temperature ranging from 40 to 50° C. and by adding the resulting reaction mixture with dicyclohexylamine.

4. The process as claimed in claim 1, wherein salt (IV) is converted again to 7-hydroxyisoflavone in an acid environment at pH ranging from 2 to 3.

5. The process as claimed in claim 1, wherein salt (IV) is converted again to 7-hydroxyisoflavone by using a water/sec-butyl alcohol/orthophosphoric acid mixture in a ratio equal to 6:3:1 by wt.

* * * * *